United States Patent [19]

Sakamoto

[11] Patent Number: 4,958,083

[45] Date of Patent: Sep. 18, 1990

[54] INSPECTING APPARATUS CAPABLE OF ACCURATELY INSPECTING AN OBJECT

[75] Inventor: Nagahiro Sakamoto, Yamanashi, Japan

[73] Assignee: Hoya Corporation, Naka-Ochiai, Japan

[21] Appl. No.: 290,037

[22] Filed: Dec. 27, 1988

[30] Foreign Application Priority Data

Dec. 29, 1987 [JP] Japan .................................. 62-333952

[51] Int. Cl.⁵ ............................................ G01N 21/88
[52] U.S. Cl. ....................................... 250/572; 356/431
[58] Field of Search ........................ 250/563, 571, 572; 356/239, 429–431

[56] References Cited

U.S. PATENT DOCUMENTS

| | | | |
|---|---|---|---|
| 4,468,120 | 8/1984 | Tanimoto et al. | 250/572 |
| 4,522,497 | 6/1985 | Ikin | 250/571 |
| 4,568,835 | 2/1986 | Imamura et al. | 250/572 |
| 4,610,541 | 9/1986 | Tanimoto et al. | 250/563 |
| 4,831,274 | 5/1989 | Kohno et al. | 250/572 |

Primary Examiner—David C. Nelms
Assistant Examiner—Stephene B. Allen
Attorney, Agent, or Firm—Ladas & Parry

[57] ABSTRACT

For inspecting an object by the use of an inspecting beam, an inspecting apparatus comprises a processing arrangement for processing a first and a second detection signal which are produced when the inspecting beam is scanned on the object and which result from a partial reflected beam and a partial transmitted beam, respectively. The second detection signal is influenced not only by a pinhole defect but also by a particle defect and might indicate a false pinhole defect. In order to remove the false pinhole defect, the processing arrangement compares the second detection signal with the first detection signal so as to judge whether or not the second detection signal indicates a pinhole defect of a size which is not smaller than that of a particle defect indicated by the first detection signal. Preferably, each of the first and the second detection signals is classified into three ranks to facilitate the above-mentioned comparison.

8 Claims, 4 Drawing Sheets

INSPECTING APPARATUS CAPABLE OF ACCURATELY INSPECTING AN OBJECT

BACKGROUND OF THE INVENTION

This invention relates to an inspecting apparatus for use in inspecting an object to detect a defect on a surface of the object. It is to be noted throughout the instant specification that description will be mainly made about a photomask blank, although this invention is applicable to a photomask or the like.

A photomask blank comprises a transparent substrate and a shading film deposited over one entire surface of the substrate. Such a photomask blank plays a very important role in fabricating a semiconductor integrated circuit device by the use of a photolithography technique. This means that defects in the photomask blank bring about serious influences on a yield of the semiconductor integrated circuit device. Accordingly, such defects on the photomask blank must be inspected and reduced to a minimum.

It is mentioned here that such defects can be classified into pinhole defects and particle defects. The pinhole defects result from undesired pinholes formed on the shading film of the photomask blank. The particle defects result from particles, such as dust and the like, undesirably adhered to the shading film of the photomask blank. The pinhole defects are more serious than the particle defects in the photomask blank because the pinhole defects directly give rise to deterioration of the yield of the semiconductor integrated circuit device. Therefore, the pinhole defects should be accurately inspected in comparison with the particle defects.

In order to inspect or detect such pinhole defects and particle defects, an inspecting apparatus has been sold by Hitachi Denshi Engineering Co., Ltd. In this inspecting apparatus, a photomask blank is scanned by a light beam of a particular wavelength to detect a reflected light beam and a transmitted light beam which are reflected on and transmitted through the photomask blank. The reflected light beam is scattered by the particle defects and results in a variation of intensity. Therefore, it is possible to detect the particle defects by monitoring the variation of intensity in the reflected light beam. On the other hand, the pinhole defects can be detected by monitoring the transmitted light beam.

According to the inventor's experimental studies, it has been found that an error very often occurs on inspecting the pinhole defects. More specifically, the transmitted light beam would have to appear in number equal to the number of the pinhole defects. However, it has been confirmed that the number of the transmitted light beams has not been equal to the number of the pinhole defects and has been greater than the latter.

SUMMARY OF THE INVENTION

It is therefore an object of the present invention to provide an inspecting apparatus which is capable of accurately inspecting defects on an object.

It is another object of the present invention to provide an inspecting apparatus of the type described, by which pinhole defects can be accurately detected on a photomask blank.

Other objects of this invention will become clear as the description proceeds.

According to this invention, there is provided an apparatus for inspecting whether or not a pinhole defect is present on an object, by the use of an inspecting beam which is partially reflected as a partial reflected light beam on the object and which is partially transmitted as a partial transmitted light beam through the object. The apparatus comprises first detecting means for detecting the partial reflected light beam to produce a first detection signal which is dependent on the partial reflected light beam, second detecting means for detecting the partial transmitted light beam to produce a second detection signal which is dependent on the partial transmitted light beam, and processing means coupled to the first and the second detecting means for processing the first and the second detection signals to judge whether or not the second detection signal is subjected to an influence caused by the pinhole defect.

BRIEF DESCRIPTION OF THE DRAWING

FIG. 6 shows a judgement method in a processing unit included in the inspecting apparatus illustrated in FIG. 1.

DESCRIPTION OF THE PREFERRED EMBODIMENT

Figure 1:
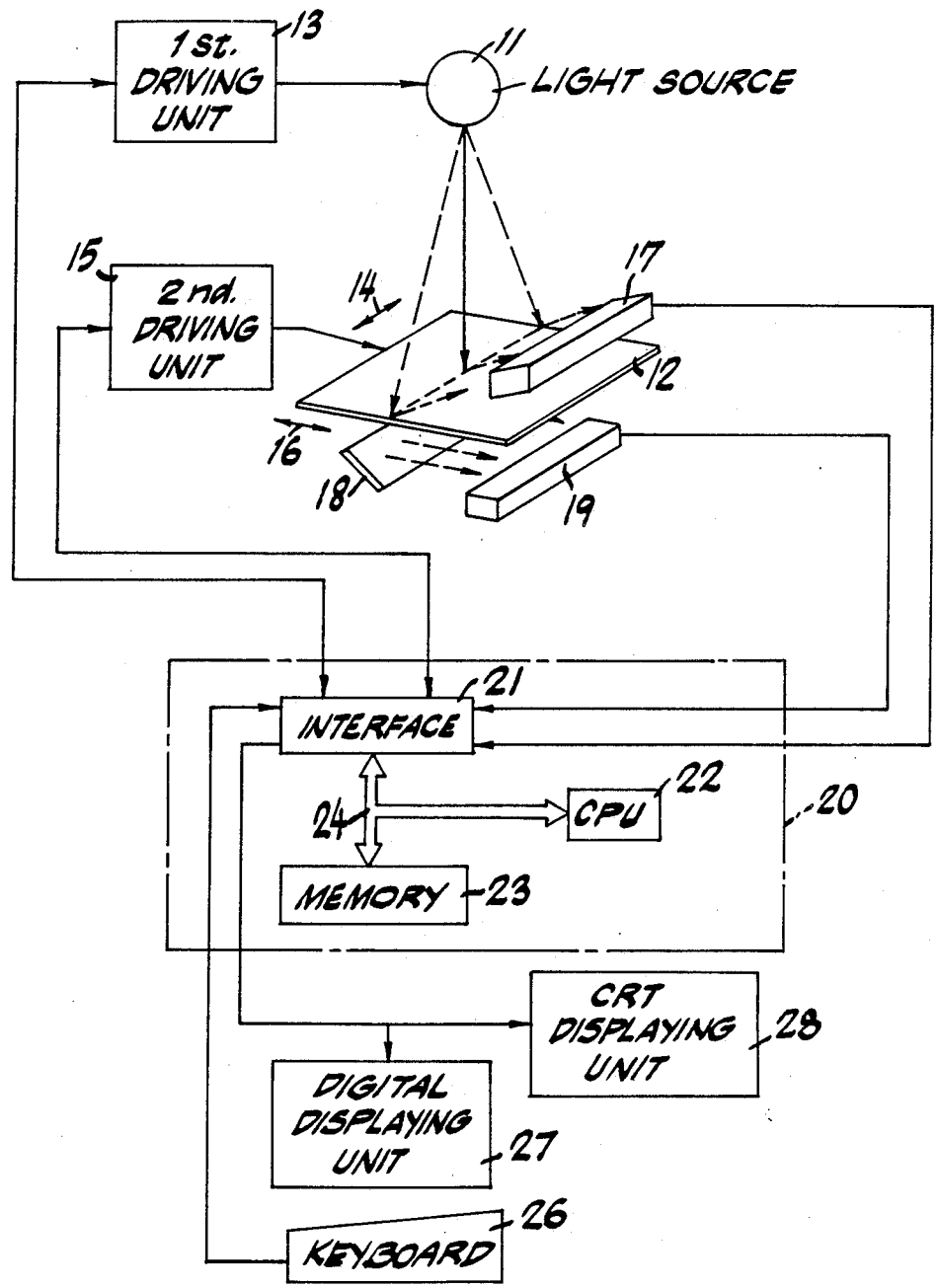
FIG. 1 shows, together with an object member, a fragmentary schematic view of an inspecting apparatus according to an embodiment of this invention.

Referring to FIG. 1, an inspecting apparatus according to an embodiment of the present invention comprises a light source 11 for emitting an inspecting beam which may be, for example, a He-Ne laser beam having a wavelength of 6328 Å. The inspecting beam is projected onto an object 12. The object 12 may be a photomask blank which will be described later. The light source 11 is driven by a first driving unit 13 to make the inspecting beam scan a top surface of the object 12 in a first predetermined direction shown by arrow 14. On the other hand, the object 12 is driven by a second driving unit 15 in a predetermined direction (shown by arrow 16) which is perpendicular to the first predetermined direction 14. As a result, the inspecting beam scans the entire top surface of the object 12 by driving the light source 11 and the object 12.

Herein, it is assumed that the inspecting beam of 6328 Å is partially transmitted as a partial transmitted light beam through the above-exemplified photomask blank and the remaining part of the inspecting beam is reflected as a partial reflected light beam on the photomask blank. The partial reflected light beam is incident onto a first detecting unit 17 while the partial transmitted light beam is reflected by a reflecting mirror 18 towards a second detecting unit 19. Each of the first and the second detecting units 17 and 19 comprises a photoelectric transducing element which is well known in the art.

Responsive to the partial reflected light beam, the first detecting unit 17 produces a first detection signal of electric voltage which has an amplitude dependent on intensity of the partial reflected light beam. Responsive to the partial transmitted light beam, the second detecting unit 19 produces a second detection signal of electric voltage which has an amplitude dependent on intensity of the partial transmitted light beam. Each of the first and the second detection signals is sent to a control unit 20.

The control unit 20 comprises an interface 21, a central processing unit (CPU) 22, and a memory 23, all of which are connected to one another through a data bus 24 in the manner illustrated in FIG. 1. The interface 21 is electrically coupled to each of the first driving, the second driving, the first detecting, and the second detecting units 13, 15, 17, and 19. This means that each of the first and the second driving units 13 and 15 drive the light source 11 and the object 12 under control of the control unit 20.

The memory 23 has a plurality of addresses numbered from a first address to an n-th address, where n may be equal to four.

The inspecting unit further comprises a keyboard 26, a digital displaying unit 27, and a CRT displaying unit 28, which are electrically coupled to the interface 21. The keyboard 26 is operable to produce a wide variety of command signals when it is manipulated by an operator. Such command signals are supplied as an input signal to the interface 21 of the control unit 20. Each of the digital and the CRT displaying units 27 and 28 is controlled by the control unit 20 and provides displays which will later be described in detail.

Figure 2:
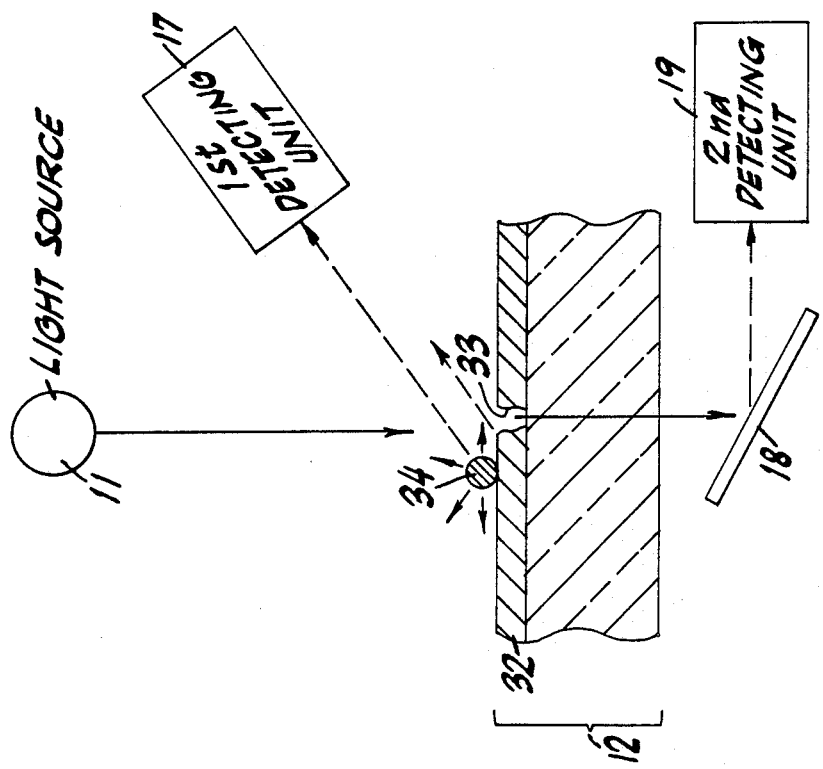
FIG. 2 shows, together with the object member, an enlarged sectional view of a part of the inspecting apparatus illustrated in FIG. 1.

Referring to FIG. 2, the object 12 comprises a transparent substrate 31 of, for example, glass and a shading film 32 of, for example, chromium deposited on a principal surface of the transparent substrate 31. The transparent substrate 31 allows the inspecting beam of 6328 Å to pass therethrough while the shading film 32 of chromium allows the inspecting beam to subtly pass therethrough. However, it is a matter of course that the shading film 32 is opaque to a light beam in the visible range which is generally used in a photolithography technique for fabricating a semiconductor integrated circuit device.

In general, defects which might occur in the photomask blank are classified as a pinhole defect 33 and a particle defect 34.

Figure 3:
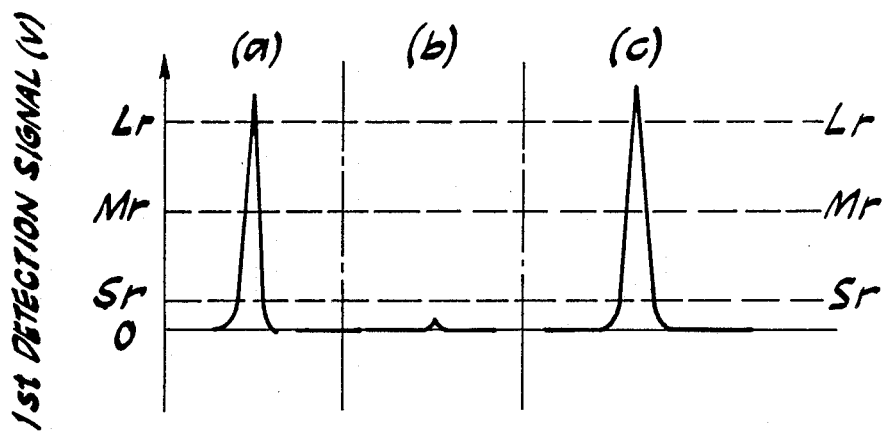
FIG. 3 is a time chart for use in describing the operation of a first detection unit included in the inspecting apparatus illustrated in FIG. 1.
Figure 4:
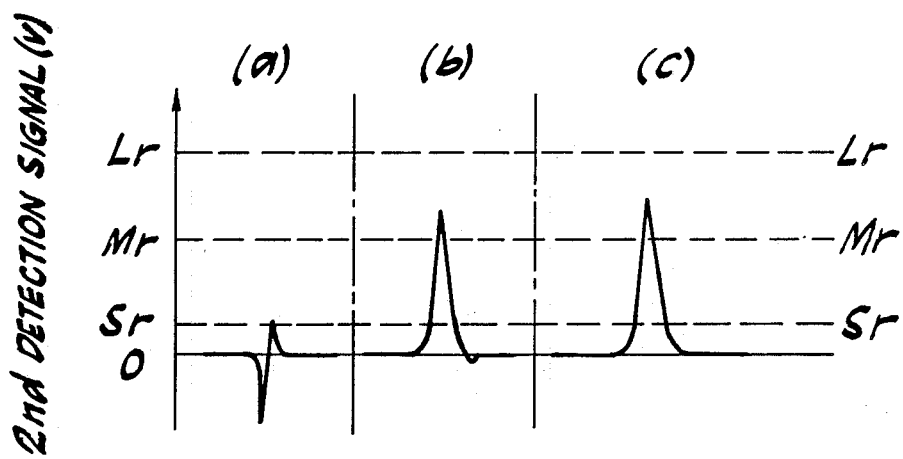
FIG. 4 is a time chart for use in describing the operation of a second detection unit included in the inspecting apparatus illustrated in FIG. 1.

Referring to FIGS. 3 and 4 together with FIG. 2, description will be directed to a relationship between the pinhole and the particle defects and the intensity or amplitudes of the reflected and the transmitted light beams. Specifically, when the inspecting beam is incident onto a part of the photomask blank which has neither the pinhole defect 33 nor the particle defect 34, each of the partial reflected and the partial transmitted light beams has reference intensity and makes the first and the second detecting units 17 and 19 produce each of the first and the second detection signals of a reference electric voltage or level which may be, for example, a zero volt, as shown in FIGS. 3 and 4.

When the inspecting beam is incident on the pinhole defect 33, the intensity of the partial transmitted light beam becomes higher than the reference intensity. As a result, the electric voltage of the second detection signal becomes higher than the reference electric voltage, as specified by levels appearing within time intervals (b) and (c) of FIG. 4.

When the inspecting beam is incident on the particle defect 34, the intensity of the partial reflected light beam becomes higher than the reference intensity and results in production of the first detection signal which has a voltage level higher than the reference electric voltage, as specified by levels appearing within time intervals (a) and (c) of FIG. 3.

At any rate, each of the partial reflected light beam and the partial transmitted light beam has a variable level or amplitude dependent on each size of the particle and the pinhole defects and varies the amplitude or level of each of the first and the second detection signals. In this connection, each amplitude or level of the first and the second detection signals is classified into three ranks with reference to first, second, and third threshold levels depicted at Lr, Mr, and Sr shown in FIGS. 3 and 4. The first threshold level Lr is determined for a defect of a large size and is higher than the second threshold level Mr determined for a defect of a middle size. The second threshold level Mr is higher than the third threshold level Sr determined for a defect of a small size. Accordingly, each of the particle and the pinhole defects may be judged as being of a large size when each of the first and the second detection signals has a level over the first threshold level Lr. In this case, each of the first and the second detection signals is classified in a highest one of the three ranks that will be specified by L.

When each of the first and the second detection signals has a level between the first and the second threshold levels Lr and Mr, both inclusive, a defect may be classified in a middle rank of the three ranks that will be specified by M.

Likewise, a defect may be classified in a lowest one of the three ranks that will be specified by S when each level of the first and the second detection signals is intermediate between the second and the third threshold levels Mr and Sr, both exclusive.

When each level of the first and the second detection signals is equal to or lower than the third threshold level Sr, such detection signals may be processed as noise. This means that an inactive region is determined by the third threshold level Sr.

Now, it has been found that the second detection signal becomes weak as compared with the reference level (0) when the first detection signal belongs to the highest rank, as specified by levels appearing within each time interval (a) of FIGS. 3 and 4 when a large size of a particle defect is scanned by the inspecting beam. In this case, it is to be noted that the second detection signal is temporarily lowered to a negative level, and is thereafter quickly changed from the negative level to a positive one, as shown in FIG. 4. Such a quick change of the partial transmitted light beam brings about occurrence of an overshoot portion in the second detection signal. Thus, there is a probability that the second detection signal has the positive level on detection of a particle defect of a large size, despite the fact that no pinhole defect is present on the photomask blank. Such a positive level of the second detection signal is erroneously regarded as occurrence of a pinhole defect in a conventional inspecting apparatus.

Under the circumstances, it is possible to avoid erroneous detection of the overshoot portion as the inactive region becomes wide. However, such a wide inactive region makes it difficult to accurately detect each defect.

With the inspecting apparatus, it is possible to avoid an error which results from a particle defect of a large size in the manner which will become clear later.

Figure 5:
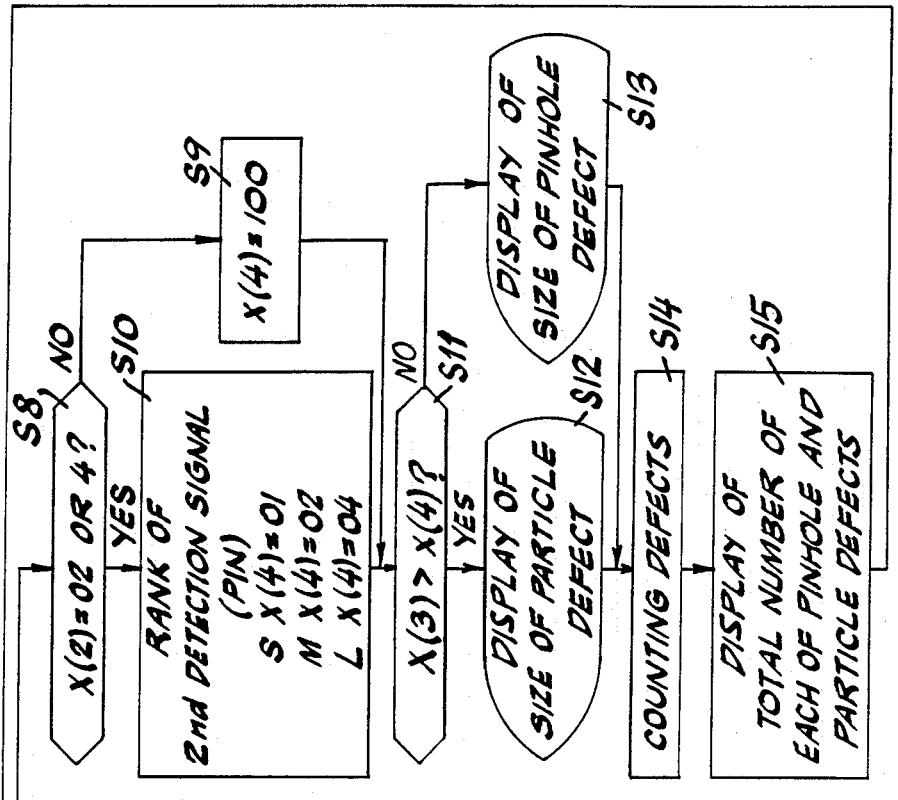
FIG. 5 is a flow chart for use in describing the operation of the inspecting apparatus illustrated in FIG. 1.

Referring to FIG. 5 together with FIGS. 1 through 4, operation of the control unit 20 will be described in detail. The top surface of the object, namely, photomask blank 12 is divided into a plurality of unit areas. The inspecting apparatus carries out inspecting operation at every one of the unit areas.

In FIG. 5, the inspecting operation begins from a first step S1 of receiving the first and the second detection signals in the CPU 22 through the interface 21. The first and the second detection signals will hereafter be collectively simply called a detection signal.

The first stage S1 proceeds to a second stage S2 at which each of the first and the second detection signals is judged by the CPU 22 to determine whether or not a defect or defects are present in the unit area in question. When any defects are present on each unit area, a number signal of "01" is written in the first address (depicted at x(1)) of the memory 23. Otherwise, a number signal of "00" is written in the first address x(1). Under the circumstances, the number signals "01" and "00" may be called a defect presence signal and a defect absence signal, respectively.

The second stage S2 is followed by a third stage S3 to judge whether or not the number signal of "00" is stored in the first address x(1). When the number signal of "00" is stored in the first address x(1), the third stage S3 returns back to the second stage S2. Otherwise, the third stage S3 proceeds to a fourth stage S4 of discriminating a species of the defect indicated by each of the first and the second detection signals.

When the first detection signal alone is received by the CPU 22 at the fourth stage S4, a number signal of "01" is written in the second address (depicted at x(2)) of the memory 23 so as to specify occurrence of a particle defect represented by PAR. Specifically, the number signal of "01" is produced when the first detection signal has a voltage higher than the reference electric voltage (0). On the other hand, a number signal of "02" is written in the second address x(2) on reception of the second detection signal alone. The number signal of "02" is produced when the second detection signal has an electric voltage higher than the reference electric voltage. Furthermore, a number signal of "04" is written in the second address x(2) when both of the first and the second detection signals have an electric voltage higher than the reference electric voltages.

The fourth stage S4 is followed by a fifth stage S5 to judge whether or not either one of the number signals "01" and "04" is stored in the second address x(2). This shows that the number signal of "02" is distinguished from the number signals of "01" and "04" at the fifth stage S5 which proceeds to a sixth stage S6 of writing a number signal of "00" in the third address (depicted at x(3)) of the memory 23.

When either one of the number signals of "01" and "04" is stored in the second address x(2), the fifth stage S5 is followed by a seventh stage S7 of classifying the first detection signal into the highest, the middle, and the lowest ranks L, M, and S with reference to the first through third threshold levels Lr, Mr, and Sr (FIG. 3). At any rate, the CPU 22 classifies the first detection signal in a selected one of the highest, the middle, and the lowest ranks at the seventh stage S7. This means that each size of the defects is determined by the CPU 22 by monitoring the content of the second address x(2). Thus, the CPU 22 may be referred to as a first determining arrangement.

When the first detection signal has a level higher than the first threshold level Lr as illustrated within the time interval (a) of FIG. 3, the number signal "04" is written as a reflection rank signal in the third address x(3) to indicate the highest rank L. When the first detection signal has a level which falls within the first and the second threshold levels Lr and Mr, the number signal of "02" is written as the reflection rank signal in the third address x(3) to indicate the middle rank M. When first detection signal has a level between the second and the third threshold levels Mr and Sr, the number signal of "01" is written as the reflection rank signal in the third address x(3) to indicate the lowest rank S. In this event, the CPU 22 compares each level of the first detection signal with the first through third threshold levels Lr, Mr, and Sr and may therefore be referred to as a first comparing arrangement. Each of the sixth and the seventh stages S6 and S7 is followed by an eighth stage S8.

At the eighth stage S8, judgement is made whether or not the second address x(2) is loaded with one of the number signals of "02" and "04".

When neither the number signal of "02" nor the number signal of "04" is stored in the second address x(2) and the number signal of "01" is stored instead of the number signals of "02" and "04", the eighth stage S8 proceeds to a ninth stage S9 at which the number signal of "00" is written in the fourth address x(4) of the memory 23.

On the other hand, when either one of the number signals "02" and "04" is loaded with the second address x(2), the eighth stage S8 proceeds to a tenth stage S10 at which the second detection signal is classified in a manner similar to that illustrated in conjunction with the first detection signal to discriminate a size of the particle defect (depicted at PAR). In any event, the second detection signal is classified in a selected one of the highest, the middle, and the lowest ranks to determine each size rank of the pinhole defect in the CPU 22. Therefore, the CPU 22 is operable to determine each size rank of the pinhole defect and may be referred to as a second determining arrangement.

More specifically, when the second detection signal has a level between the first and the second threshold levels Lr and Mr, as illustrated within the time intervals (b) and (c) of FIG. 4, the number signal of "02" is written as a transmission rank signal in the fourth address x(4) to indicate the middle rank M.

When the second detection signal has a level between the second and the third threshold levels Mr and Sr, as shown within the time interval (a) of FIG. 4, the number signal of "01" is written as the transmission rank signal in the fourth address x(4) to indicate the lowest rank S.

When the second detection signal has a level higher than the first threshold level Lr, the number signal of "04" is written as the transmission rank signal in the fourth address x(4) to indicate the highest rank L. In this event, the CPU 22 serves to compare the level of the second detection signal with the first through third threshold levels and may be referred to as a second comparing arrangement. Each of the ninth and the tenth stages S9 and S10 is followed by an eleventh stage S11.

At the eleventh stage S11, the content of the third address x(3) is compared by the CPU 22 with that of the fourth address x(4) to decide whether or not the size of the particle defect is greater than the size of the pinhole defect. In other words, the number signal of the third address x(3) is compared with that of the fourth address x(4).

Temporarily referring to FIG. 6 in addition to FIGS. 1 and 5, the CPU 22 gives a first degree of priority (depicted at P1 in FIG. 6) when the size of the particle defect is greater than the size of the pinhole defect. In this event, the pinhole defect may be recognized as a false pinhole defect, as illustrated in conjunction with FIGS. 3 and 4 even when the pinhole defect is indicated by the second detection signal. Therefore, a twelfth stage S12 follows the eleventh stage S11 so as to display presence of the particle defect.

On the other hand, a second degree of priority P2 is given when the size of the particle defect (PAR) is equal to or smaller than that of the pinhole defect (PIN). This shows that the pinhole defect is never a false pinhole defect but a true pinhole defect, even when presence of the particle defect is indicated by the first detection signal. Therefore, presence of the pinhole defect is displayed at a thirteenth stage S13.

With this structure, it is possible to prevent a false pinhole defect from being displayed on the CRT display 28.

Each of the eleventh and the thirteenth stages S12 and S13 is followed by a fourteenth stage S14 at which each of the pinhole and the particle defects 33 and 34 is counted in number at every rank S, M, and L.

The fourteenth stage S14 is followed by a fifteenth stage S15 at which the total number of each of the pinhole and the particle defects is memorized in the memory 23 and is displayed on the digital and the CRT displaying units 27 and 28. Subsequently, the sixteenth stage S16 returns back to the second stage S2.

Thus, the inspecting operation is carried out over all of the unit areas. As a result, it is possible to accurately provide information related to the defects of the shading film 32 with reference to the digital and the CRT displaying units 27 and 28.

While the present invention has thus far been described in connection with only one embodiment thereof, it will readily be possible for those skilled in the art to put this invention into practice in various other manners. For example, the object may be a magnetic disk, a photomask blank with a resist, and others. The present invention is applicable to various kinds of photomask blanks comprising different shading films. In this case, a wavelength of the inspecting beam should be selected such that the inspecting beam is partially transmitted through the shading films.

What is claimed is:

1. An apparatus for inspecting whether or not a defect is present on an object, by the use of an inspecting beam which is partially reflected as a partial reflected light beam on said object and which is partially transmitted as a partial transmitted light beam through said object, said defect being classifiable as a pinhole defect or a particle defect, said partial transmitted light beam being subjected to an undesirable influence by said particle defect depending upon the size of said particle defect, said undesirable influence appearing as an overshoot of said partial transmitted light beam, said apparatus comprising:

first detecting means for detecting said partial reflected light beam to produce a first detection signal which is dependent on said partial reflected light beam;

second detecting means for detecting said partial transmitted light beam to produce a second detection signal which is dependent on said partial transmitted light beam; and processing means coupled to said first and said second detecting means for processing said first and said second detection signals to detect whether or not said overshoot of the partial transmitted light beam appears on the basis of said first and said second detection signals and thereby to inspect occurrence of said defect on said object.

2. An apparatus as claimed in claim 1, said first detection signal being representative of intensity of said partial reflected light beam, wherein said processing means comprises:

classifying means coupled to said first detecting means for classifying said first detection signal into a plurality of ranks to produce a reflection rank signal representative of each of said ranks of said first detection signal; and judging means coupled to said second detecting and said classifying means for judging from said second detection and said reflection rank signals whether or not said second detection signal is subjected to said influence.

3. An apparatus as claimed in claim 1, said second detection signal being representative of intensity of said partial transmitted light beam, wherein said processing means comprises:

classifying means coupled to said second detecting means for classifying said second detection signal into a plurality of ranks to produce a transmission rank signal representative of each of said ranks of said second detection signal; and judging means coupled to said first detecting and said classifying means for judging from said first detection and said transmission rank signals whether or not said second detection signal is subjected to said influence.

4. An apparatus as claimed in claim 1, said first detection signal being representative of intensity of said partial reflected light beam, said second detection signal being representative of intensity of said partial transmitted light beam, wherein said processing means comprises:

first classifying means coupled to said first detecting means for classifying said first detection signal into a first set of ranks to produce a reflection rank signal representative of each rank of said first set;

second classifying means coupled to said second detecting means for classifying said second detection signal into a second set of ranks to produce a transmission rank signal representative of each rank of said second set;

judging means coupled to said first and said second classifying means for judging from said reflection and said transmission rank signals whether or not said second detection signal is subjected to said influence.

5. An apparatus as claimed in claim 1, wherein said object is a photomask which has a shading zone for shading said inspecting beam.

6. An apparatus as claimed in claim 1, wherein said object is a photomask blank which has a shading layer for shading said inspecting beam.

7. Apparatus for inspecting an object for pinhole defects comprising means for producing an inspecting light beam which is partially reflected as a partial reflected light beam and which is partially transmitted as a partial transmitted light beam through said object, first detecting means for detecting said partial reflected light beam to produce a first detection signal which is dependent on said partial reflected light beam;

second detecting means for detecting said partial transmitted light beam to produce a second detection signal which is dependent on said partial transmitted light beam; and processing means coupled to said first and said second detecting means for determining pinhole defects in the object, the object also being capable of having particle defects in addition to said pinhole defects, which particle defects produce false signals indicating the erroneous presence of pinhole defects when said particle defects exceed a given size, said processing means including means for detecting the production of false pinhole defect signals produced by particle defects and removing the false pinhole defect signals so that only signals indicative of actual pinhole defects are produced.

8. An apparatus as claimed in claim 7 wherein the first detection signal produced by a particle defect above a determined size causes an overshoot in the second detection signal representing a false pinhole defect, said means for detecting false pinhole defect signals including means for correlating values in said first signal representing the presence of particle defects with values in said second signal representing the presence of pinhole defects to detect and eliminate overshoots in the second signal.

* * * * *